US00PP08614P

United States Patent [19]

Dickson

[11] Patent Number: Plant 8,614

[45] Date of Patent: Mar. 1, 1994

[54] ROSE PLANT DICREVIVAL

[75] Inventor: Patrick Dickson, Newtownards, Ireland

[73] Assignee: Bear Creek Gardens, Inc., Medford, Oreg.

[21] Appl. No.: 26,315

[22] Filed: Mar. 2, 1993

[51] Int. Cl.[5] ..... A01H 5/00

[52] U.S. Cl. ..... Plt./9

[58] Field of Search ..... Plt. 9, 10

*Primary Examiner*—James R. Feyrer
*Assistant Examiner*—Bruce R. Campell
*Attorney, Agent, or Firm*—Klarquist, Sparkman, Campbell, Leigh and Whinston

[57] ABSTRACT

A miniature rose easily propagated by softwood or hardwood cuttings; having dark green, glossy, disease-resistant foliage; and constant display of bright, deep pink flowers during the growing season.

1 Drawing Sheet

The present invention relates to a new and distinct variety of rose plant of the miniature class which was originated by me by crossing the variety DICmagic, with the variety of DICmerlin.

An objection of this breeding was to obtain a compact growing variety with a high yield of small flowers and foliage.

This new variety evidences these characteristics and the following unique combination of characteristics which are outstanding in the new variety and which distinguish it from its parents, as well as from all other varieties of which I am aware:

1. Dark green, glossy, disease-resistant foliage;
2. Can be easily propagated from hardwood or softwood cuttings;
3. Has very bright, deep pink flowers; and
4. Blooms constantly and profusely throughout the growing season.

Asexual reproduction of this new variety by softwood cuttings, as performed at Wasco, Calif., and Newtownards, County Down, Northern Ireland, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—DICmagic.

*Pollen parent.*—DICmerlin.

Classification:

*Botanical.*—*Rosa hybrida.*

*Commercial.*—Miniature.

FLOWER

Observations made from specimens grown in garden environments in Somis, Calif., and Newtownards, County Down, Northern Ireland.

Blooming habit: Continuous.

Bud:

*Size.*—½ inch when the petals start to unfurl.

*Form.*—Short, pointed ovoid.

*Color.*—When sepals first divide, bud color is Red Group 52A. When half blown, the upper and lower sides of the petals are Red Group 52A.

*Sepals.*—Color: Green Group 138B with a reddish cast. Surface texture: Covered in fine hairs. There are three lightly appendaged sepals. There are two unappendaged sepals with hairy edges.

*Receptacle.*—Color: Green Group 137A often with a reddish cast. Shape: Funnel. Size: Small (¼×¼ inch). Surface: Smooth.

*Peduncle.*—Length: Short (1 to 1¼ inches). Surface: Glandular. Color: Bronzy. Strength: Stiff, erect.

Bloom:

*Size.*—Small. Average open size is 1½ inches.

*Borne.*—Several together. If in clusters: Flat.

*Stems.*—Short, strong (8–10 inches).

*Form.*—When first open: High centered. Permanence: Flattens, all petals curl.

*Petalage.*—Number of petals under normal conditions: 15–20.

*Color.*—The upper and reverse sides of the petals are Red Group 52A. The base of each petal has a very small (⅛×⅛ inch) white half moon at the point of attachment. The major color on the upper side is Red Group 52A.

*Variegations.*—Occasional white streak on the interior petals.

*Discoloration.*—The general tonality at the end of the first day: No change. At the end of the third day, Gradual fading to Red Group 52C.

*Fragrance.*—Slight.

Petals:

*Texture.*—Thin.

*Shape.*—Deltoid.

*Form.*—Tips slightly recurved, edges slightly quilled.

*Arrangement.*—Imbricated, with few petaloids in the center.

*Persistence.*—Drop off cleanly.

*Lastingness.*—On the plant: Short (4 days). As a cut flower: not tested.

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Red.

*Stigmas.*—Color: Greenish white.

Form: Bush.

Growth: Very vigorous, dwarf, upright, branching.

Foliage:

*Number of leaflets on normal mid-stem leaves.*—5.

*Size.*—Small (2½ inches×2 inches).

*Quantity.*—Abundant.

*Color.*—New foliage: Reddish turning dark green quickly. Old foliage: Dark green (Green Group 139A).

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Smooth but with many glands.

*Stipules.*—Short, serrated, bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Many. On laterals from main canes: Many.

*Form.*—Short, hooked downward.

*Color when young.*—Red.

Small prickles:

*Quantity.*—On main stalks: Many. On laterals: Many.

*Color.*—Red.

I claim:

1. A new and distinct variety of rose plant of the miniature class, substantially as herein shown and described, characterized particularly as to novelty by the unique combination of its ease of propagation by softwood or hardwood cuttings; its dark green, glossy, disease-resistant foliage; its bright, deep pink flowers; and its constant display of flowers during the growing season.

* * * * *

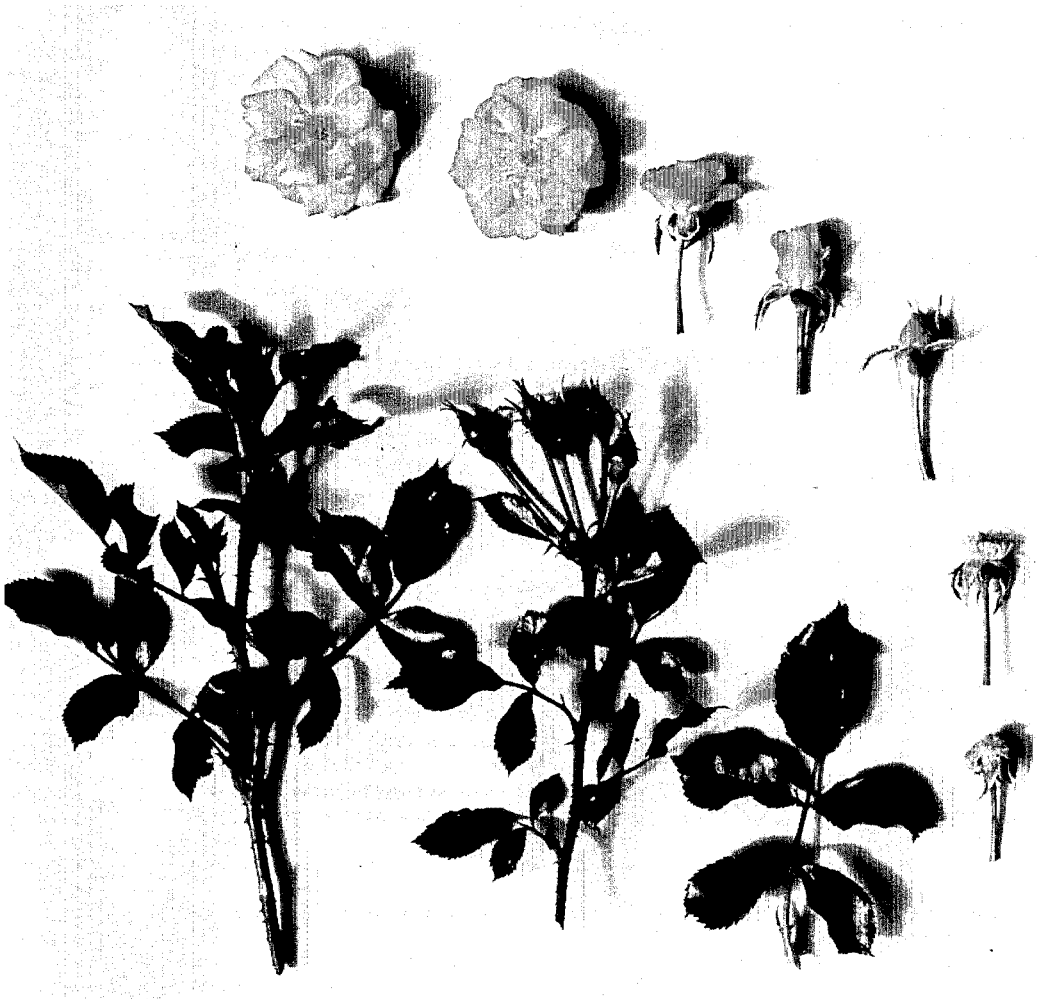
DICrevival